United States Patent [19]
Alexander et al.

[11] Patent Number: 5,632,750
[45] Date of Patent: May 27, 1997

[54] DEVICE FOR ASSISTING CHILDBIRTH

[75] Inventors: Gary E. Alexander; Robert L. diBenedetto, both of Baton Rouge, La.

[73] Assignee: Medisys Technologies, Inc., Baton Rouge, La.

[21] Appl. No.: 413,125

[22] Filed: Mar. 29, 1995

Related U.S. Application Data

[63] Continuation-in-part of Ser. No. 250,054, May 27, 1994, which is a continuation-in-part of Ser. No. 36,560, Mar. 25, 1993, Pat. No. 5,318,573, which is a continuation-in-part of Ser. No. 982,016, Nov. 24, 1992, Pat. No. 5,217,467, which is a continuation of Ser. No. 851,068, Mar. 13, 1992, which is a continuation-in-part of Ser. No. 522,592, May 14, 1990, Pat. No. 5,122,148.

[51] Int. Cl.$^6$ ........................................ A61B 17/42
[52] U.S. Cl. ........................ 606/122; 606/1; 606/119; 606/121
[58] Field of Search ....................... 606/1, 119, 121, 606/122

[56] References Cited

U.S. PATENT DOCUMENTS

| | | | |
|---|---|---|---|
| 1,782,814 | 11/1930 | Froehlich | 606/122 |
| 4,875,482 | 10/1989 | Hariri et al. | 606/122 |
| 5,122,148 | 6/1992 | Alexander | 606/122 |
| 5,207,687 | 5/1993 | Bernon | 606/119 |
| 5,217,467 | 6/1993 | Alexander | 606/122 |
| 5,318,573 | 6/1994 | Alexander | 606/1 |

FOREIGN PATENT DOCUMENTS

2925386  1/1981  Germany .............. 606/122

*Primary Examiner*—Robert A. Hafer
*Assistant Examiner*—Benjamin Koo
*Attorney, Agent, or Firm*—Roy, Kiesel & Tucker

[57] ABSTRACT

A device to assist in removing a fetus from a woman's birth canal during childbirth is provided. The device includes a pliable, elongated cylinder with at least one end to fit over the head of the fetus, insertion wands for positioning the cylinder over the head of the fetus, wand sheaths which hold the insertion wands in place, and a drawstring attached at the open end. An insertion sleeve is used to compress the open end of the cylinder so that the cylinder can be inserted into the mother. An application cone is provided for spreading the open end of the cylinder and guiding it over the head during application. The cylinder is constructed so that as it is pulled from the end opposite the open end, the cylinder will axially grip the head of the fetus and extract the fetus from the mother. A method of using the device is also described.

8 Claims, 9 Drawing Sheets

DEVICE FOR ASSISTING CHILDBIRTH

CROSS-REFERENCE

This is a continuation-in-part application of a U.S. patent application Ser. No. 08/250,054, filed on May 27, 1994, which is a continuation-in-part application of a U.S. patent application Ser. No. 08/036,560, filed on Mar. 25, 1993, now U.S. Pat. No. 5,218,573, which is a continuation-in-part application of U.S. patent application Ser. No. 07/982,016, filed on Nov. 24, 1992, now U.S. Pat. No. 5,217,467, which was a file wrapper continuing application of U.S. patent application Ser. No. 07/851,068, filed on Mar. 13, 1992, now abandoned, which was a continuation-in-part application of U.S. patent application Ser. No. 07/522,592, filed on May 14, 1990, now U.S. Pat. No. 5,122,148.

BACKGROUND OF THE INVENTION

1. Field of the Invention

This invention relates in general to obstetric devices, and more particular to devices useful in removing the fetus during vaginal delivery.

1. Prior Art

Today's state of the art obstetrics utilizes various procedures to assist in instances of difficult vaginal deliveries. These procedures basically fall into three categories: version, Caesarian and forceps-assisted delivery. In the case of severe cephalo-pelvic disproportion, placenta previa, vaso previa, and other contraindications to vaginal delivery, the "C-Section," whether classic or low transverse, remains the mainstay procedure. However, it has long been recognized that to the extent that C-Section deliveries can be successfully avoided, statistical maternal and fetal benefits will be realized. Even the non-difficult vaginal delivery can benefit from non-traumatic assists.

Many problems may develop during delivery which require assistance from the attending obstetrician to successfully remove the baby from the birth canal. One such problem results from the presenting part of the baby, usually its head, descending too slowly. This is particularly true in the case of the primigravida mother. Even with a completely dilated and effaced cervix, and an adequate pelvis, a fetus might refuse to descend beyond station "+1", especially when the mother is suffering from contraction exhaustion. Slow descent remains a problem even with an assist from administration of oxytocin (Pitocin). The problem of slow descent can also be exacerbated by anesthesia, especially epidural anesthesia, which frequently produces induced non-beneficial partial atony of the engaged and dedicated muscles. Such partial atony frequently results in non-beneficial, and sometimes hazardous, prolongation of labor.

Forceps are limited by the stage of delivery at which they may be safely applied. Station "+1" is considered mid-pelvis and in the usual case is considered too high for a forceps-assisted delivery. The risks to the fetus with forceps application at this level are extreme. Forceps cannot be safely used until the presenting part is at least at station "+2", and preferably between stations "+2" and "+3", which is the floor of the perineum. Modern obstetrics has not developed an alternative to the use of forceps when an assisted natural delivery is indicated, such as when the fetus is consistently exhibiting late decelerations of heartbeat following contractions or is exhibiting non-variability of the baseline heartbeat rate.

Obstetrical forceps are typically, in their various types, two-bladed instruments which are blindly inserted one blade at a time in a hopefully temporal-cheek position and then articulated together before assisting traction is applied. Actual traction is exerted slightly below or underneath the mandible. Traction applied with forceps is point concentrated and slippage of the forceps is increased because of natural lubrication, refusal of the fetal skull to conform to existing forceps design, and other known myriad of variables that vary from one fetus-to-pelvis physical relationship to another.

Even proper positioning of the forceps can result in harm to the fetus. For example, in instances of minimal cephalo-pelvic disproportion, the insertion of one blade of the forceps can exacerbate any slight deficiency in birth canal adequacy. In addition the softness, or pliability, of the fetal skull, coupled with the existence of sutures which separate the plates of the skull, render the skull susceptible to trauma associated with metal forceps assisted deliveries.

In an attempt to alleviate the potential trauma of forceps, vacuum extractors have seen some use. Devices which use cloth or other pliable materials which envelope the fetal head have been developed. However, because these devices are pliable insertion of these devices can be problematic or slow. What is needed is a device for assisting childbirth which is safe for the mother and the fetus and which overcomes the shortcomings of the prior art.

OBJECTS OF THE INVENTION

It is therefore an object of this invention to provide an assisting device for childbirth which can safely perform substantially all of the functions of forceps and vacuum extractors without the risks inherent in the use of these devices.

Another object of this invention is to provide an assisting device for childbirth that is easy to use and reduces the risk of injury to the fetus during childbirth.

Still another object of this invention is to provide an assisting device for childbirth that can be quickly applied to the head of the fetus by the attending physician.

Still other objects and advantages of this invention shall become apparent from the ensuing descriptions of the invention.

SUMMARY OF THE INVENTION

A device for assisting the delivery of a fetus is provided. The device includes a sock-like elongated cylindrical member having an open first end sized to fit over and surround the fetal head. Two or more pliable sheaths are spaced around the elongated member and attached at its open end. Semi-rigid insertion wands fit into the sheaths and are used to push the elongated member over the fetal head. The insertion wands are attached at their proximal ends to a rigid hollow insertion handle, so that the operator the apparatus can apply force to all of the wands by simply pushing on the insertion handle. An application cone engages the fetal head and guides the elongated member's open over the fetal head. Pressure is maintained on the cone by the use of an application rod which is attached to the application cone. The proximal end of the application rod fits through and protrudes from the insertion handle. An insertion sleeve is used to compress the open first end of the elongated member and the insertion wands for the initial insertion of the device into the introitus. The elongated member also includes a drawstring which keeps the elongated member over the fetal head until axial gripping of the fetal head by the elongated member can be initiated.

It is an advantage of the invention that it can be operated by only one person, with surgical shears being the only additional equipment required.

It is a further advantage of the invention that the apparatus is of minimal thickness and fits easily between the fetal head and the birth canal.

DETAILED DESCRIPTION

Figure 1:
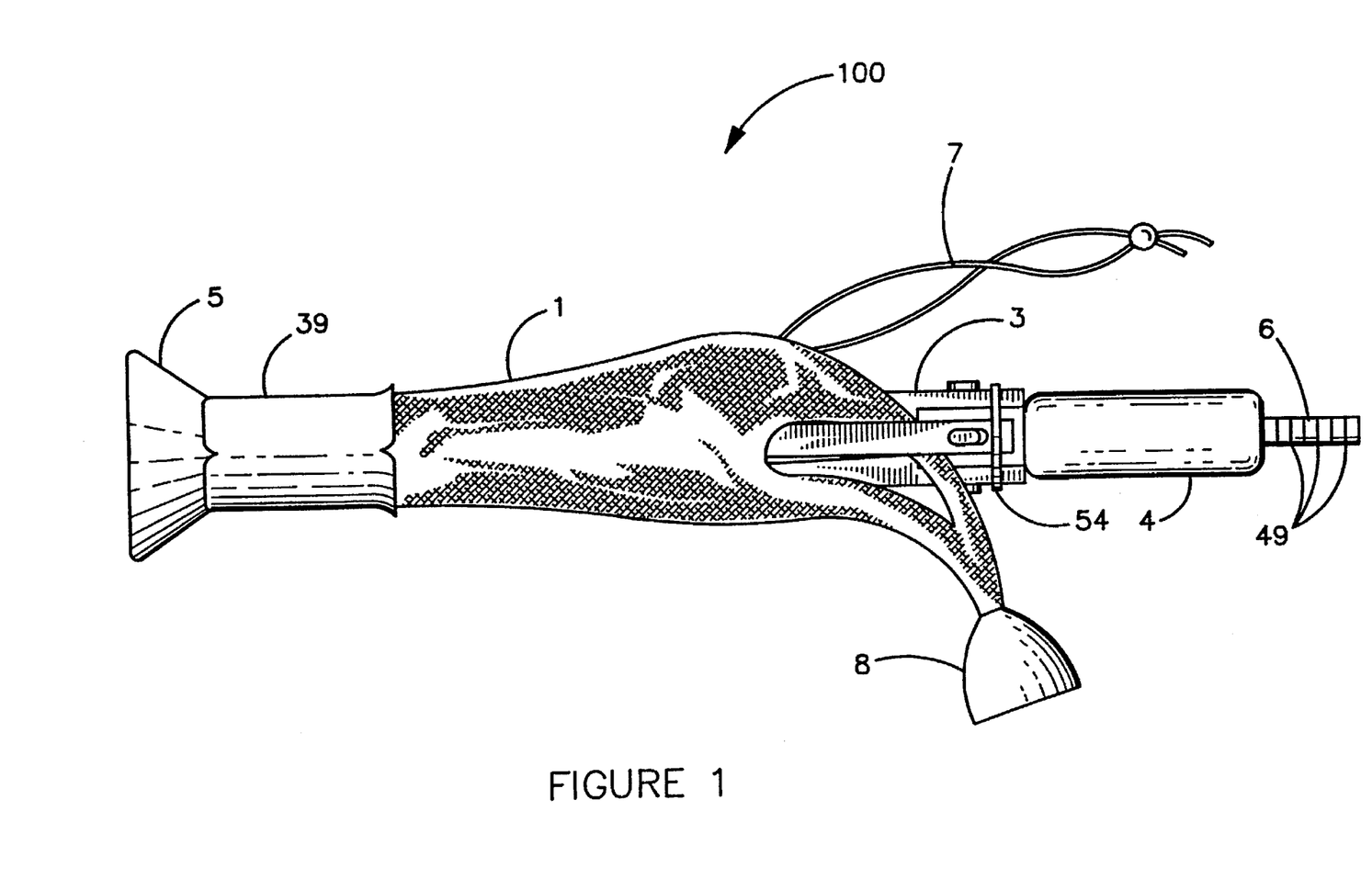
FIG. 1 is a perspective view of the apparatus as it appears when shipped and ready for use.

FIG. 1 is a perspective view of the device for assisting childbirth 100 with all components. The device includes elongated member 1, wand sheaths 2 (not shown), insertion wands 3, insertion handle 4, application cone 5, application rod 6, restricting means 7, and traction handle 8.

Figure 2:
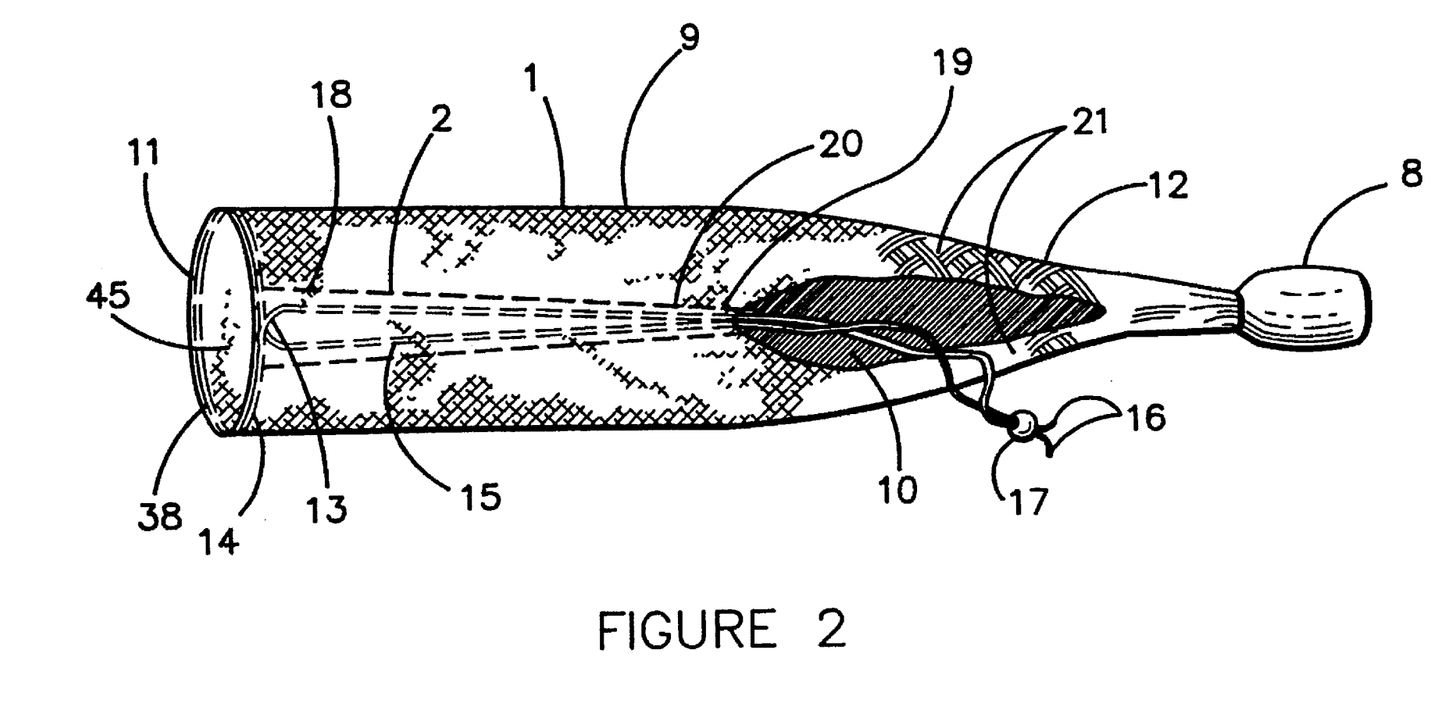
FIG. 2 is a perspective view of the elongated member forming part of this invention.

Referring to FIG. 2, elongated member 1 is depicted. Elongated member 1 includes open first end 11 and second end 12 which are connected by passageway 45. Elongated member 1 will be formed of a braid material. As depicted in FIG. 2, for the preferred embodiment a double-layered elongated member is formed by extruding a continuous cylindrical member and then folding the cylindrical member so that outer layer 9 and inner layer 10 are formed. One could terminate the braid material by cutting it at open first end 11 and sewing or binding together the fibers. However, it is preferred to terminate the braid material by folding it to form a double-layered member. Compared to a single-layered member, a double-layer member exhibits enhanced axial gripping qualities and is easier to manufacture.

The braid material is constructed by loosely weaving series of strands in an over and under manner. In the embodiment depicted the series use monofilament strands, such as fishing line, with a thickness of six/one-thousandths of an inch. The strands are in a parallel series of five each; however, one skilled in the art could construct the device with more or fewer strands in each series. Also, although in the embodiment depicted the braid material is constructed of monofilament fibers, one skilled in the art could construct the braid material from any material or fibers which would allow elongated member 1 to exhibit axial gripping.

Restricting means 13 for tightening said open first end about the neck and head of the fetus is generally located at open first end 11. Restricting means 13 includes drawstring sleeve 14, which can be an enveloping structure such as a nylon cloth tube, and drawstring 15. Although in the embodiment depicted, drawstring sleeve 14 is a nylon tube, one could route drawstring 15 through loops attached to open first end 11, could weave drawstring 15 through the braid material, or could use any other means capable of causing drawstring 15 to cooperate with open first end 11 so as to tighten open first end 11 around the fetal head when drawstring 15 is pulled.

Drawstring ends 16 are held together by fastener 17. As can be seen in FIG. 2, drawstring 15 is looped around open first end 11 within drawstring sleeve 14 such that drawstring looped portion 38 constitutes part of restricting means 13. Thus, as drawstring 15 is pulled, generally from the fastener 17, drawstring looped portion 38 will decrease in size, which in turn will decrease the size of the opening at open first end 11.

A plurality of wand sheaths 2 are also provided, although in FIG. 2 only one such sheath is shown in phantom. Wand sheaths 2 are positioned between outer layer 9 and inner layer 10. Drawstring 15 can be routed from open first end 11 to second end 12 via one of the wand sheaths 2. In a particularly preferred embodiment, four wand sheaths 2 are positioned equidistantly about elongated member 1. Each wand sheath 2 is a pliable elongated nylon pocket with terminal end 18 and receiving end 19. Wand sheath 2 need only be attached to elongated member 1 at one point, although one skilled in the art could provide more attachment points.

In the embodiment depicted in FIG. 2, wand sheath 2 will be attached to elongated member 1 at sheath attachment point 20, which is generally where the braid material of elongated member 1 is no longer woven, which is also the beginning of pigtails 21. Wand sheath 2 is only attached to one layer of elongated member 1, so as to promote axial gripping secondary to traction and to allow the device to be peeled from the fetal head if the device has to be removed before delivery. Although sheaths 2 are depicted as extending to the openings formed by pigtails 21, elongated member 1 could be completely closed at second end 12, and sheaths 2 could be attached at buttonhole slits made in elongated member 1.

As seen in FIG. 2, the point where elongated member 1 is no longer woven branches out into a plurality of pigtail branches 21 which are joined together at traction handle 8. Traction handle 8 is used to hold pigtails 21 together and provides a place for the operator, generally a physician, to grab hold and exert a pulling force. Traction handle 8 can be of any shape suitable for gripping.

Figure 3A:
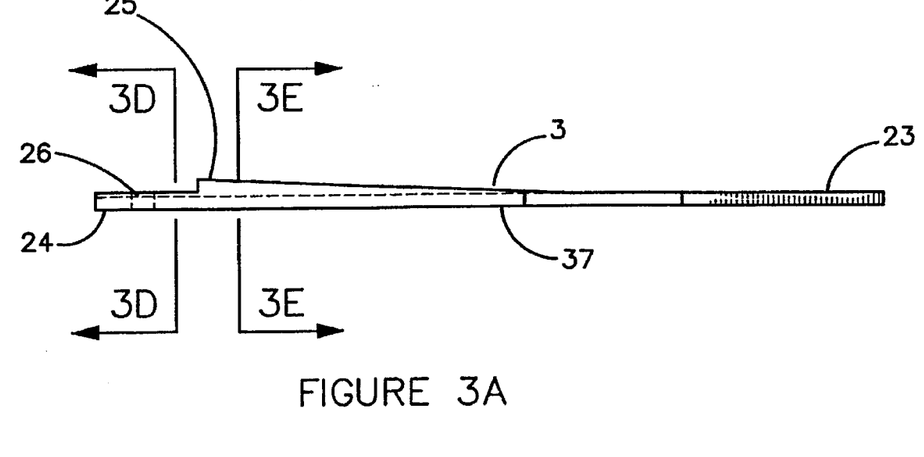
FIG. 3A shows a side view of a single insertion wand forming part of this invention.

Referring now to FIGS. 3A–3E, the preferred embodiments of insertion wands 3 and insertion handle 4 are depicted. Insertion wand 3 is semi-rigid and made of high impact plastic. Insertion wand 3 has distal end 23 and proximal end 24. As shown in FIG. 3A, insertion wand 3 presents a profile twice as thick at handle stop 25 as at wand proximal end 24. Insertion wand 3 has aperture 26 between handle stop 25 and wand proximal end 24.

Figure 3B:
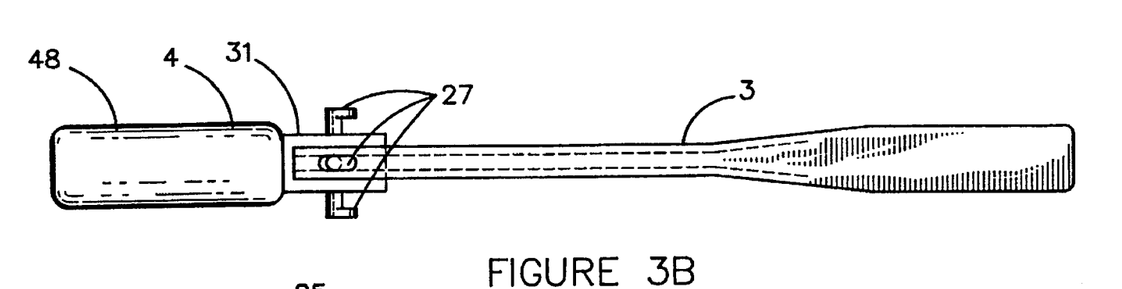
FIG. 3B shows the insertion handle with a single attached insertion wand forming part of this invention.

Referring to FIG. 3B, insertion handle 4 is a hollow tube having exterior surface 31, grip section 48, and a tunnel (not shown) running along its entire length. A plurality of rigid catches 27 are distributed equidistantly around exterior surface 31. In the embodiment shown, there are four catches 27, although one skilled in the art could practice the invention with two or more catches and a corresponding number of wands and sheaths. Each catch 27 is L-shaped so as to engage aperture 26 on insertion wand 3 so that insertion wand 3 will remain attached to insertion handle 4 as the operator pushes the device 100 into the introitus of the mother using insertion handle 4. The device may also include elastic band 54, as shown in FIG. 1, to ensure that insertion wands 3 remain attached to insertion handle 4.

Figure 3C:
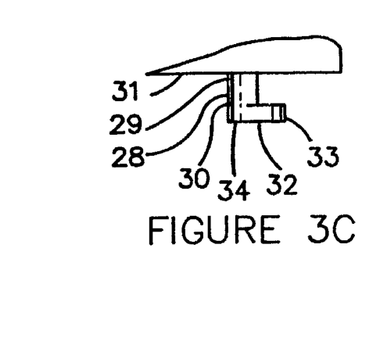
FIG. 3C is an enlarged view of a single catch forming part of this invention.

FIG. 3C is an enlarged view of catch 27 showing radial section 28 which is attached to exterior surface 31 at radial section proximal end 29. Radial section 28 extends radially outward from section proximal end 29 and terminates at radial section distal end 30. Radial section 28 has a length approximately equal to the thickness of insertion wand 3 at wand proximal end 24.

Catch 27 also has axial section 32 which has free end 33 and corner end 34. Corner end 34 is attached to radial section distal end 30 at about a 90° angle. Axial section 32 extends from corner end 32 in a direction toward wand distal end 23 and parallel to the long axis of insertion handle 4 and terminates in free end 33. As shown in FIG. 3B, axial section 32 is shaped to match with the shape of aperture 26 in insertion wand 3.

Figure 3D:
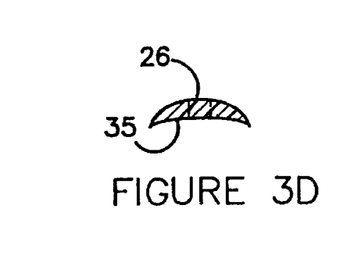
FIG. 3D is a sectional view of an insertion wand taken along view line 3D in FIG. 3A.

FIG. 3D is a sectional view of insertion wand 3 along view line 3D of FIG. 3A. Shown are aperture 26 and first arcuate surface 35. First arcuate surface is shaped to match with the curvature of exterior surface 31 of insertion handle 4.

Figure 3E:
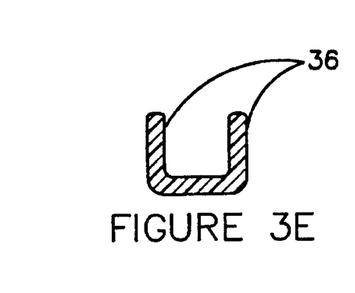
FIG. 3E is a sectional view of an insertion wand taken along view line 3E in FIG. 3A.

FIG. 3E is a sectional view of insertion wand 3 along view line 3E of FIG. 3A. Handle stop 25 is formed by two raised portions 36. As shown by FIG. 3A, raised portions 36 taper down in size along the length of insertion wand 3 away from wand proximal end 24. Insertion wand is substantially flat by wand midpoint 37 so that insertion wand will be easier to fit between the fetal head and the wall of the birth canal. At wand distal end 23, insertion wand 3 must be thin enough to be pliable, yet thick enough to retain longitudinal strength.

Figure 4:
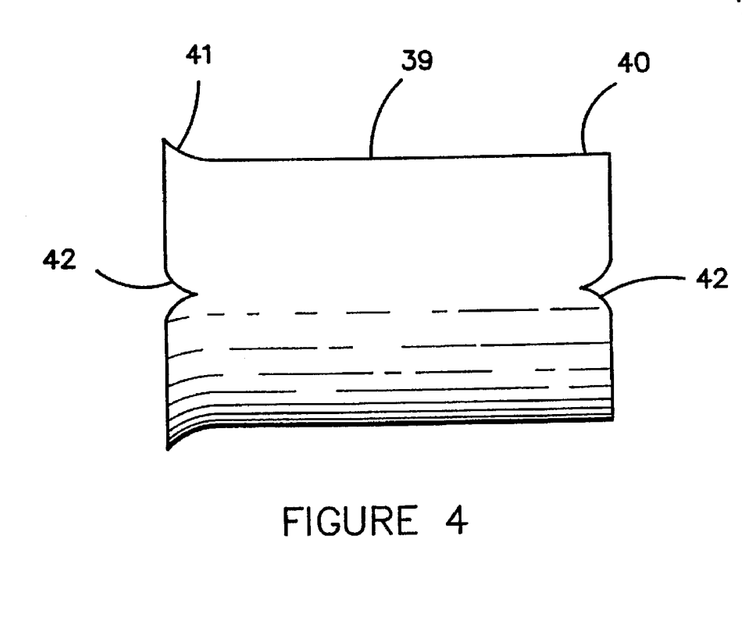
FIG. 4 shows a side view of a preferred embodiment of the insertion sleeve forming part of this invention.

FIG. 4 depicts a preferred embodiment of insertion sleeve 39, which is a hollow pliable tubular member of clear plastic. Insertion sleeve has sleeve first end 40 which may be straight or may be flared radially inward. Sleeve first end 40 is the end which will be introduced into the introitus of the mother. Sleeve second end 41 may be flared radially outward as shown, or be straight like sleeve first end 40. The size of insertion sleeve 39 is adapted such that insertion sleeve 39 will fit over open first end 11 of elongated member 1, with insertion wands 3 contained therein, and constrict said open first end to a size sufficient to allow insertion of open first end 11 into the birth canal of the mother.

Insertion sleeve 39 is made of a material which may be cut easily with surgical shears. Insertion sleeve 39 may also include shear notches 42, which are cutouts at sleeve first end 40 and second end 41.

Figure 5:
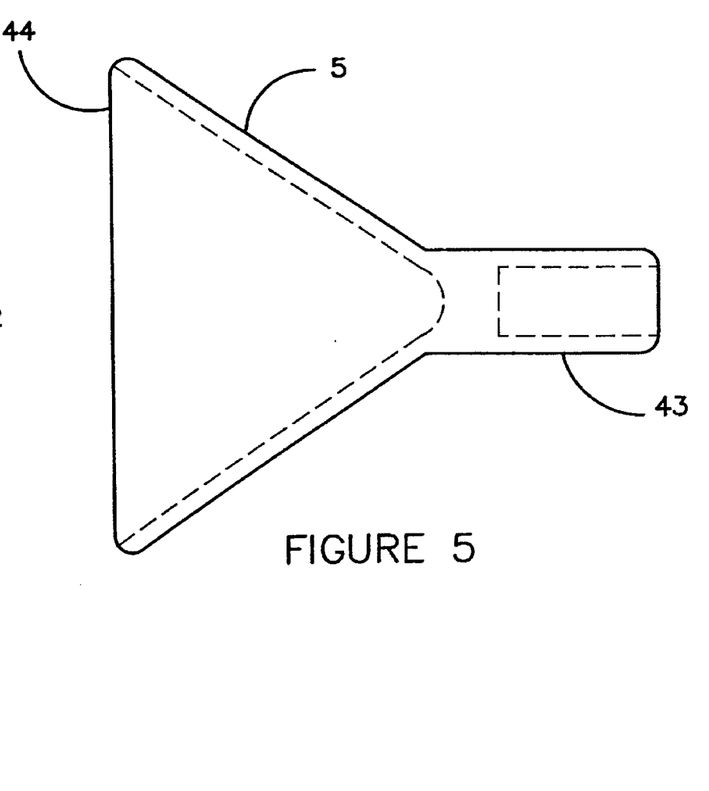
FIG. 5 shows a side view of the application cone forming part of this invention.

FIG. 5 depicts application cone 5, which is a pliable resilient member having cone attachment end 43 and cone open end 44. Cone 5 is adapted to fit within open first end 11 and passageway 45 of elongated member 1. Cone 5 serves to guide open first end 11 over the fetal head.

Figure 6:
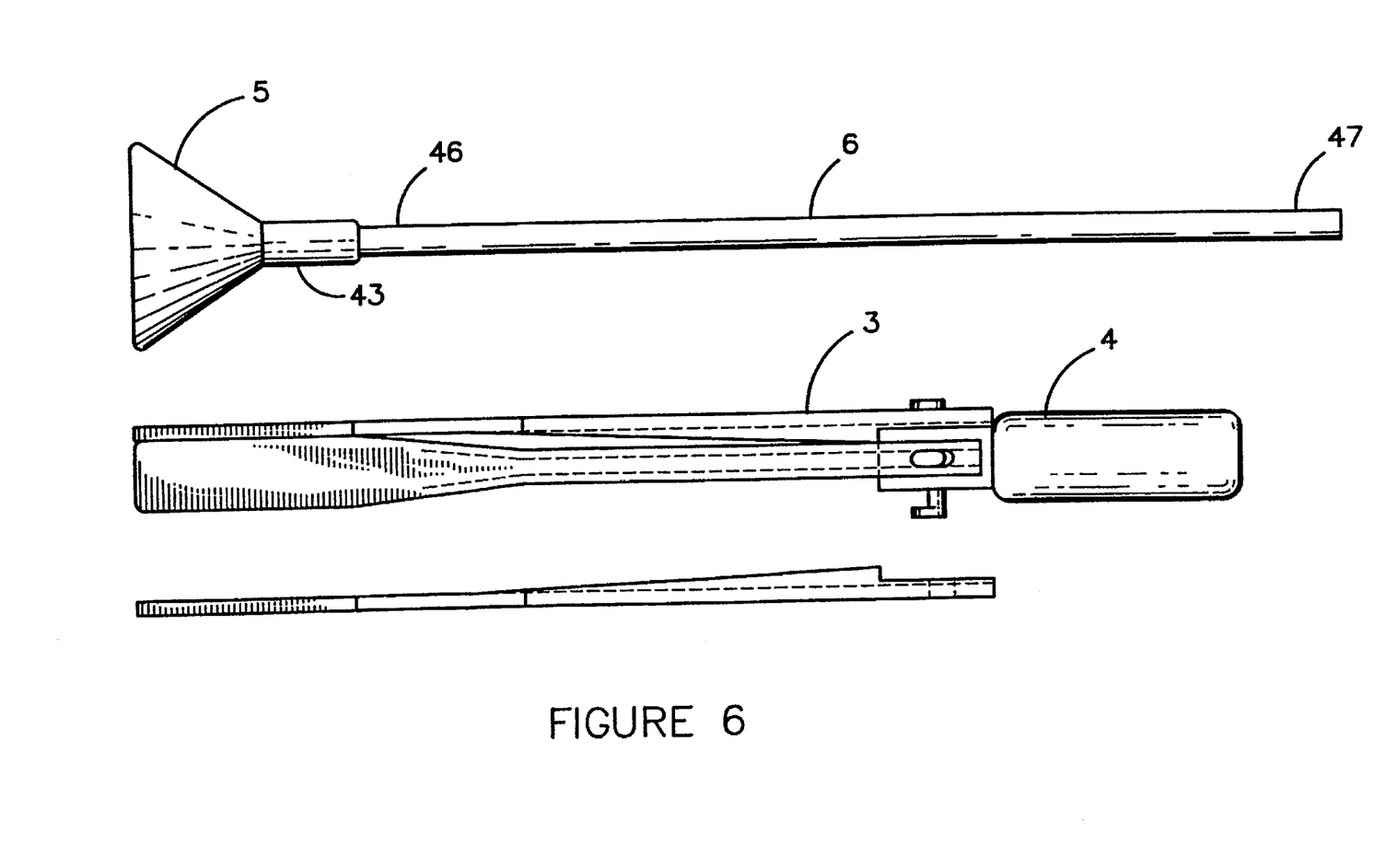
FIG. 6 shows the application cone and application rod forming part of this invention. Also depicted are the insertion handle and insertion wands.

FIG. 6 depicts application cone 5 attached to application rod 6. Application rod 6 is a rigid or semi-rigid rod with a circular cross-section. Application rod 6 has rod distal end 46 and rod proximal end 47. As shown by FIG. 6, application rod 6 has a length greater than the connected combination of insertion wands 3 and insertion handle 4 so that when device 100 is assembled as shown in FIG. 1, rod proximal end 47 will protrude from insertion handle 4. Rod distal end 46 is attached to cone 5 at cone attachment end 43. Application rod 6 is made so that, at least at its proximal end 47, application rod 6 will slidably fit through the tunnel of insertion handle 4. As shown in FIG. 1, graduation markings 49 may be placed on application rod 6 near rod proximal end 47. Graduation markings 49 will assist the operator in determining when the device has been properly placed over the fetal head.

Figure 7:
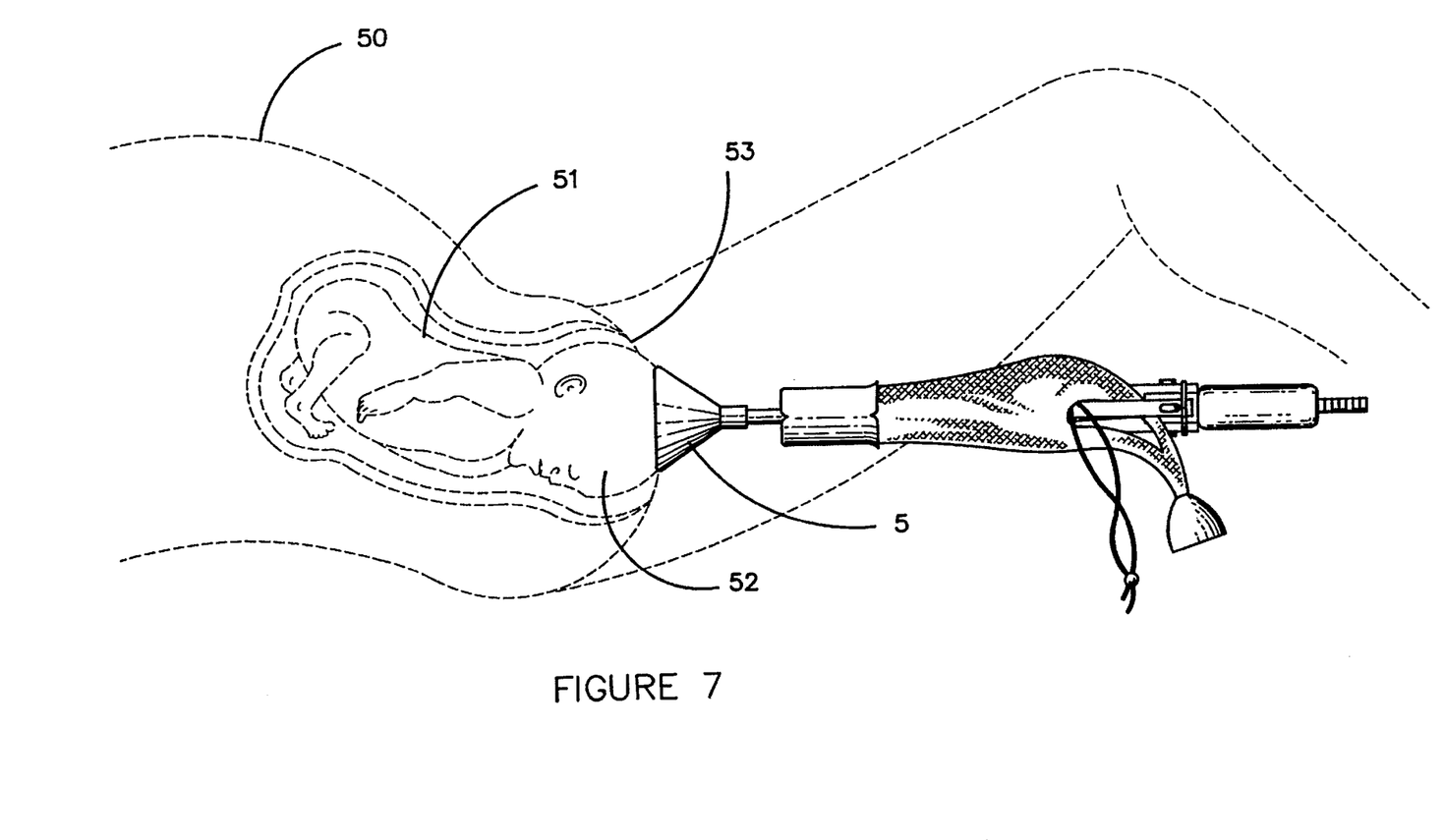
FIGS. 7–10 are cut-away views of a mother with a fetus. The figures depict various stages of the use of the apparatus in vaginal delivery.

The operation of the device will now be described with reference to FIGS. 7–10. FIGS. 7–10 are cut-away views of mother 50 with fetus 51 ready for delivery. The operator of the device, usually a physician, will prepare device 100 for insertion so that device 100 is configured as shown in FIG. 1. The operator folds cone 5 and inserts cone 5 into introitus 53 so that cone 5 can open up and engage fetal head 52 as shown in FIG. 7.

Figure 8:
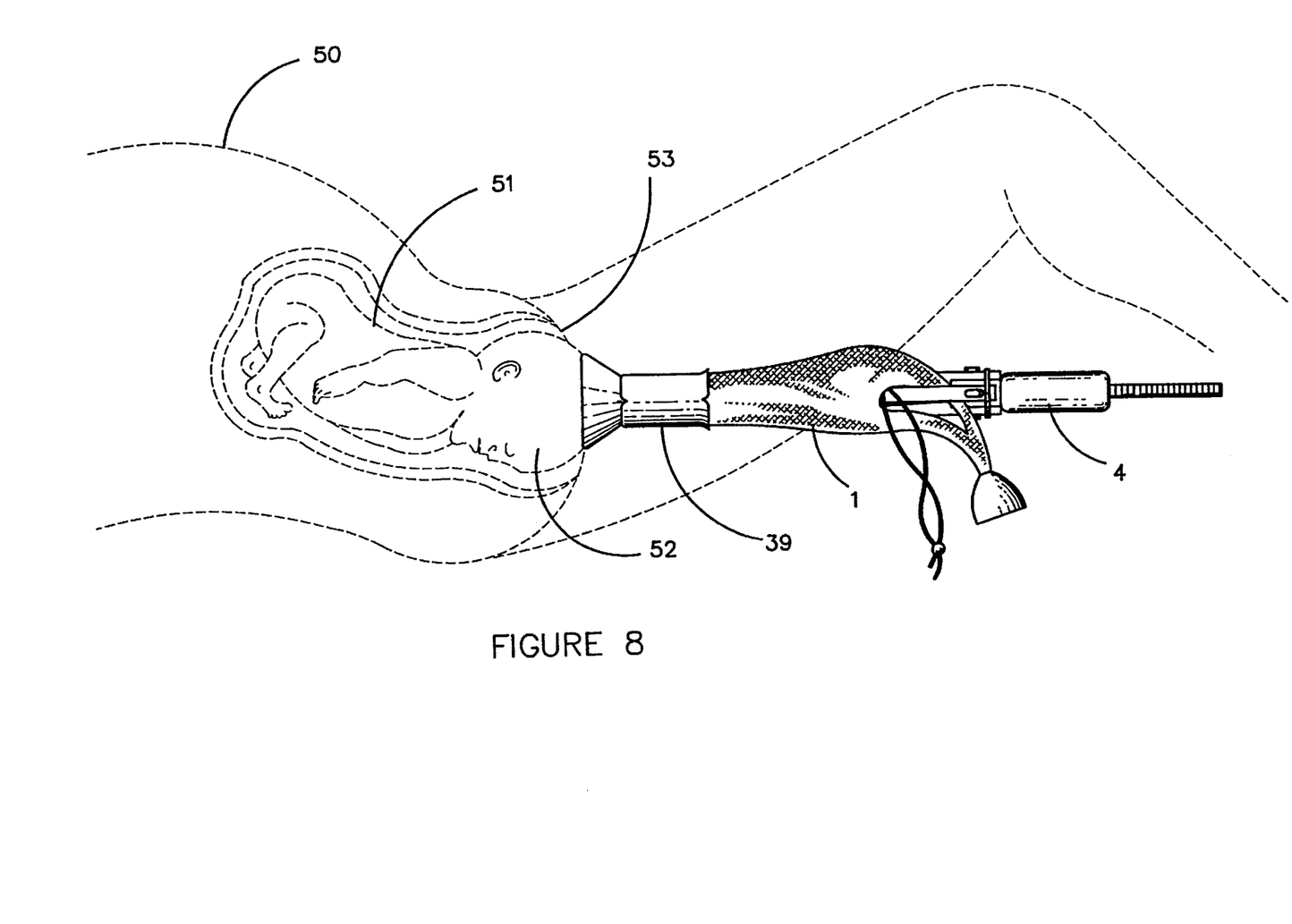

Ensuring that open first end 11 and insertion wands 3 are contained within insertion sleeve 39, as shown in FIG. 1, the operator next inserts at least a portion of insertion sleeve 39 into introitus 53, as shown in FIG. 8. The operator can now, by applying force into the birth canal at insertion handle 4, slide elongated member 1 through insertion sleeve 39 into the birth canal of said mother. The operator then slides insertion sleeve 39 rearward out from introitus 53 and cuts and removes insertion sleeve 39.

Figure 9:
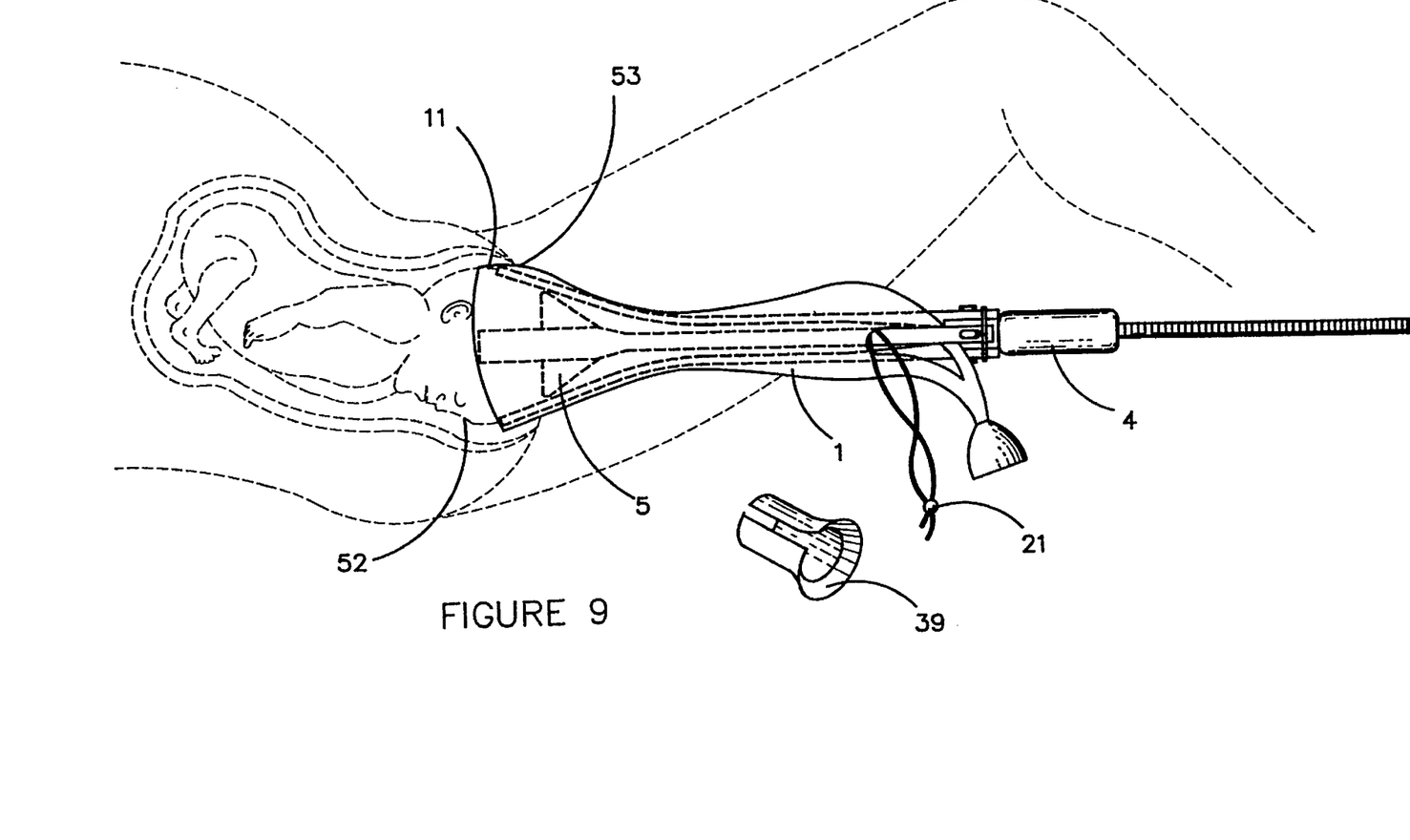

As depicted in FIG. 9, the operator next pushes forward (into the birth canal) on insertion handle 4 while maintaining cone 5 engaged against head 52 so that cone 5 guides open first end 11 of elongated member 1 over head 52. Although open first end 11 is optimally positioned below the mentum head 52 prior to traction being applied, it is only necessary that open first end 11 be below the widest cross-section of head 52, as presented. Pulling on fastener 21, the operator tightens restricting means 13 so that open first end 11 is fitted about head 52 while continuing to apply forward force to insertion handle 4.

The operator pulls rearward on insertion handle 4 to remove insertion handle 4 with attached insertion wands 3 while maintaining tension on restricting means 13. Continuing to maintain tension, the operator removes application rod 6 with cone 5.

Figure 10:
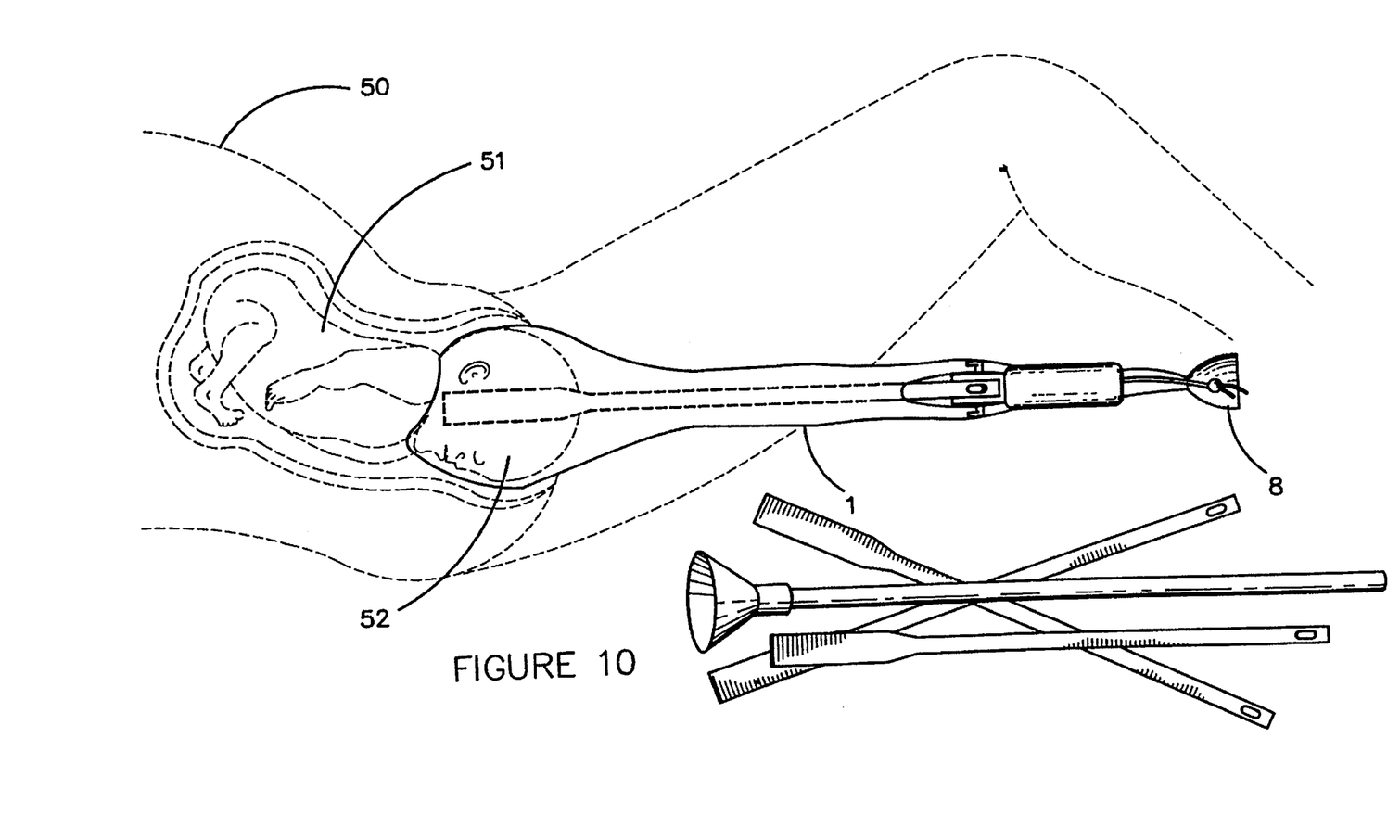

Elongated member 1 is now over head 52 as shown in FIG. 10. The operator pulls rearward on traction handle 8 while maintaining tension on restricting means 13 so that the braid material of elongated member 1 will axially grip head 52 as shown in FIG. 10. Once axial gripping is initiated, the operator no longer needs to maintain tension on restricting means 13. The operator continues to pull on traction handle 8 to extract fetus 51 from mother 50 and complete delivery. Constant or intermittent traction can be applied to facilitate the head's passage through the birth canal.

Device 100 can be adapted to facilitate various complications of delivery. For example, depending on the presentation of the fetus, the operator can attach insertion wands 3 of varying lengths onto insertion handle 4 so as to properly place open first end 11 over the fetal head.

The invention should be understood to assist in the delivery of any type of fetus, not only human fetuses. In other words, the embodiments disclosed would also be applicable to veterinary obstetrics in deliveries of such mammals as horses, cattle, and sheep.

There are, of course, other alternate embodiments which are obvious from the foregoing descriptions of the invention which are intended to be included within the scope of the invention as defined by the following claims.

I claim:

1. A device for assisting the delivery of a fetus, comprising:
   (1) an elongated member having an open first end and a second end connected by a passageway into which the head of a fetus may be fit, said open first end being adapted to receive said head therein so that said open first end surrounds said head;
   (2) a plurality of wand sheaths, equidistantly disposed along said elongated member, each said wand sheath having a terminal end and a receiving end, wherein said receiving end is attached to said elongated member;
   (3) an insertion wand corresponding to each said wand sheath, each said insertion wand being a semi-rigid member having a proximal end and a distal end and being adapted such that said insertion wand may be received within said receiving end of said sheath;
   (4) a rigid hollow elongated insertion handle, said insertion handle having a tunnel therethrough and being adapted such that said proximal end of each said insertion wand is removably attached to said insertion handle;
   (5) a pliable resilient application cone having an attachment end and an open end, said cone being adapted to fit within said elongated member open first end and said elongated member passageway;
   (6) an application rod having a distal end and a proximal end and having a length greater than the connected combination of said insertion wands and said insertion handle, said rod distal end being attached to said cone attachment end, said rod proximal end being adapted to slidably fit through said insertion handle tunnel;
   (7) a pliable tubular insertion sleeve, said insertion sleeve being adapted such that said sleeve will fit over said elongated member open first end and constrict said open first end to a size sufficient to allow insertion of said open first end into the birth canal of the mother, said sleeve being further adapted so as to be cut with surgical shears and removed after said insertion of said elongated member open first end; and
   (8) restricting means cooperating with said open first end of said elongated member for tightening said open first end about said head.

2. The apparatus in claim 1, wherein said insertion wand has an aperture near said insertion wand proximal end and said insertion handle is a hollow tube having an exterior surface with a plurality of rigid catches distributed equidistantly around said exterior surface, each said catch comprising:
   (i) a radial section having a proximal end and a distal end said radial section proximal end being attached to said exterior surface, said radial section extending radially outward from said exterior surface and terminating in said distal end, said radial section having a length approximately equal to the thickness of said insertion wand proximal end;
   (ii) an axial section having a free end and a corner end, said corner end being attached to said radial section distal end at about a 90° angle, said axial section extending from said corner end in a direction toward said application cone and parallel to the long axis of said insertion handle, and terminating in said free end, said axial section being adapted to fit through said insertion wand aperture.

3. The apparatus of claim 2 wherein said elongated member further comprises an outer layer and an inner layer and said elongated member is constructed of a braid material comprising loosely interwoven series of monofilament strands.

4. The apparatus of claim 3 wherein said restricting means comprises a drawstring with two ends and a looped portion, said looped portion extending at least partially about said open first end of said elongated member, said drawstring extending along said elongated member away from said open first end of said elongated member, and terminating in said drawstring ends, said drawstring being adapted so that as said first and second ends of said drawstring are pulled, said elongated member open first end is tightened about said head.

5. The apparatus of claim 4 further comprising a traction handle attached to said second end of said elongated member, said traction handle being adapted such that the operator of said apparatus can exert a pulling force at said elongated member second end in order to initiate and maintain axial gripping of said elongated member about said head.

6. The apparatus in claim 5, wherein said insertion sleeve further comprises:
   (i) first and second ends, said insertion sleeve second end being flared radially outward; and
   (ii) shear notches at said first and second ends of said insertion sleeve.

7. The apparatus in claim 6, further comprising graduation markings on said application rod near said rod proximal end.

8. A method of assisting the delivery of a fetus during birth, the method comprising the steps of:
   (a) providing an apparatus for insertion into the introitus of a mother, said apparatus including: an elongated member made of braid material and having an open first end and a second end connected by a passageway into which the head of a fetus may be fit; a plurality of wand sheaths, equidistantly disposed along said elongated member, each said wand sheath having a receiving end attached to said elongated member and a terminal end; an insertion wand corresponding to each said wand sheath, each said insertion wand being a semi-rigid member having a proximal end and a distal end and being adapted such that said insertion wand may be received within said receiving end of said sheath; an insertion handle, said insertion handle having a tunnel therethrough and being adapted such that said proximal end of each said insertion wand is removably attached to said insertion handle; a pliable resilient application cone having an attachment end and an open end, said cone being adapted to fit within said elongated member open end and said elongated member passageway; an application rod having a distal end and a proximal end and having a length greater than said insertion wands, said distal end being attached to said cone attachment end, said proximal end being adapted to slidably fit through said insertion handle tunnel; a hollow pliable tubular insertion sleeve adapted such that said sleeve will fit over said elongated member open first end and constrict said open first end to a size sufficient to allow insertion of said open first end into the birth canal of the mother; and restricting means cooperating with said open first end of said elongated member for tightening said open first end about said head;
   (b) folding said cone and inserting said cone into the introitus so that said cone will open up and engage said fetal head;
   (c) inserting said insertion sleeve containing said elongated member open first end and said wand distal ends into said introitus;

(d) sliding said elongated member through said sleeve into the birth canal of said mother by applying a forward force, into the birth canal, to said insertion handle;

(e) sliding said sleeve out of said introitus and cutting and removing said sleeve while maintaining a forward force on said insertion handle;

(f) pushing said insertion handle forward into the birth canal while maintaining said cone engaged against said head so that said cone guides said open first end of said elongated member over said head until said open first end is below the largest cross-section of said head, as presented;

(g) tightening said restricting means so that said open first end is fitted about said head while continuing to apply forward force to said insertion handle;

(h) removing said insertion handle, said wands and said cone while maintaining tension on said restricting means;

(i) pulling rearward on said elongated member second end while maintaining tension on said restricting means so that said braid material elongated member axial grips said head;

(j) ceasing to maintain tension on said restricting means;

(k) delivering said fetus.

* * * * *